US008861741B2

(12) United States Patent
Sugawara

(10) Patent No.: US 8,861,741 B2
(45) Date of Patent: Oct. 14, 2014

(54) ACOUSTIC DEVICE, NOISE CONTROL METHOD, NOISE CONTROL PROGRAM, AND RECORDING MEDIUM

(75) Inventor: Keitaro Sugawara, Saitama (JP)

(73) Assignee: Pioneer Corporation, Kanagawa (JP)

( * ) Notice: Subject to any disclaimer, the term of this patent is extended or adjusted under 35 U.S.C. 154(b) by 401 days.

(21) Appl. No.: 13/263,289

(22) PCT Filed: Apr. 15, 2009

(86) PCT No.: PCT/JP2009/057569
§ 371 (c)(1),
(2), (4) Date: Oct. 6, 2011

(87) PCT Pub. No.: WO2010/119521
PCT Pub. Date: Oct. 21, 2010

(65) Prior Publication Data
US 2012/0027220 A1 Feb. 2, 2012

(51) Int. Cl.
*A61F 11/06* (2006.01)
*G10K 11/178* (2006.01)
*G10K 11/16* (2006.01)

(52) U.S. Cl.
CPC ...... *G10K 11/1784* (2013.01); *G10K 2210/511* (2013.01); *G10K 2210/108* (2013.01); *G10K 2210/128* (2013.01)
USPC ......................................... 381/71.1; 381/71.6

(58) Field of Classification Search
USPC .............................. 381/71.1–71.8, 94.1–94.9
See application file for complete search history.

(56) References Cited

U.S. PATENT DOCUMENTS

2010/0260345 A1* 10/2010 Shridhar et al. ............. 381/71.1

FOREIGN PATENT DOCUMENTS

| | | |
|---|---|---|
| JP | 06-282282 | 10/1994 |
| JP | 06-282283 | 10/1994 |
| JP | 06-308976 | 11/1994 |
| JP | 07-311580 | 11/1995 |
| JP | 10-335960 | 12/1998 |
| JP | 2006-264502 | 10/2006 |
| JP | 2008-213755 | 9/2008 |

OTHER PUBLICATIONS

International Search Report, PCT/JP2009/057569, Jul. 7, 2009.

* cited by examiner

*Primary Examiner* — Vivian Chin
*Assistant Examiner* — Ammar Hamid
(74) *Attorney, Agent, or Firm* — Young & Thompson

(57) ABSTRACT

When the signal level of a signal AOD, to which a cancellation signal CND of ACD is added, is larger than the signal level of ACD, a rate of change calculation part 173 calculates the maximum value (=1) as a rate of change parameter for showing that the degree of noise cancellation should be made highest. When the signal level of AOD, to which CND of ACD is added, is smaller than the signal level of ACD, the rate of change calculation part 173 calculates a change parameter rate to show that the larger the difference between both the signal levels are, the lower the degree of the noise cancellation becomes. A cancellation signal generation part 175 then generates CND and transmits it to an addition part 171 while taking the values of the change parameter rate into consideration. As a result, proper noise control can be easily performed.

5 Claims, 5 Drawing Sheets

ACOUSTIC DEVICE, NOISE CONTROL METHOD, NOISE CONTROL PROGRAM, AND RECORDING MEDIUM

TECHNICAL FIELD

The present invention relates to an acoustic device, to a noise control method, and to a noise control program, and also relates to a recording medium upon which the noise control program is recorded.

BACKGROUND ART

From the past, acoustic devices that replay audio contents, and that output replayed audio from speakers, have often been mounted to moving bodies such as vehicles and so on. Due to this, it has been possible for users to enjoy replayed audio contents even in the spaces within the bodies of the moving bodies.

Now, a moving body is generally provided with an engine or the like that generates drive power. The operating sound of such an engine or the like constitutes extraneous noise from the point of view of listening to the reproduction of audio contents in the space within the moving body, and in particular it is often the case that the operating noise of such an engine is very loud.

Due to this, techniques of various sorts have been proposed as methods for controlling noise in the space within a moving body. One such technique is a technique of determining whether or not to perform control operation for active noise cancellation, according to the level of influence of the noise upon the audio sound (i.e. upon the sound of the contents being replayed) on the basis of a noise level that is obtained based upon the result of sound pickup within the vehicle passenger compartment (refer to Patent Document #1: hereinafter termed the "prior art example").

PRIOR ART DOCUMENTS

Patent Documents

Patent Document #1: Japanese Laid-Open Patent Publication 1994-282282.

SUMMARY OF THE INVENTION

Problems to be Solved by the Invention

Since with the technique of the prior art example, as described above, it is arranged to determine whether or not to perform control operation for active noise cancellation, accordingly the sound which the listener hears changes over discontinuously due to changeover between execution and non-execution of such control operation, and sometimes it may happen that a sense of discomfort to the listener is created. Moreover, during the actual active noise cancellation control, due to sound reflection inside the passenger compartment and variation of the air transmission function because of changing of the people riding in the vehicle and so on, it becomes necessary to perform large scale signal processing at high quality in order to guess with good accuracy what level of influence upon the reproduced sound of the audio contents that is being listened to by the listeners within the passenger compartment is being experienced due to noise and due to noise cancellation.

Due to this, a technique is desired that can supply to a listener a comfortable environment for listening to replayed contents in a simple manner. To respond to this requirement is considered as being one problem that the present invention must solve.

The present invention has been conceived in the light of the considerations described above, and takes as its object to provide a new acoustic device and a new noise control method, which can perform appropriate noise control in a simple manner.

Means for Solving the Problems

Considered from a first standpoint, the present invention is an acoustic device that outputs audio from a speaker to a predetermined space, comprising: an addition means that, by adding together a first audio signal from a sound source and a noise cancellation signal, calculates a second audio signal to be supplied to said speaker; a detection means that detects a certain relationship between the signal level of said first audio signal and the signal level of said second audio signal; a sound pickup means that picks up sound that has arrived at a predetermined position within said predetermined space; and a generation means that generates said noise cancellation signal by referring to the result of detection by said detection means and to the result of sound pickup by said sound pickup means.

And, considered from a second standpoint, the present invention is a noise control method used by an acoustic device that outputs audio from a speaker to a predetermined space, comprising: an addition process of, by adding together a first audio signal from a sound source and a noise cancellation signal, calculating a second audio signal to be supplied to said speaker; a detection process of detecting a certain relationship between the signal level of said first audio signal and the signal level of said second audio signal; a sound pickup process of picking up sound that has arrived at a predetermined position within said predetermined space; and a generation process of generating said noise cancellation signal by referring to the result of detection by said detection process and to the result of sound pickup by said sound pickup process.

Moreover, considered from a third standpoint, the present invention is a noise control program, wherein it causes a calculation means to execute a noise control method according to the present invention.

Furthermore, considered from a fourth standpoint, the present invention is a recording medium, wherein a noise control program according to the present invention that can be read by a calculation means is recorded thereupon.

EMBODIMENTS FOR CARRYING OUT THE INVENTION

Figure 1:
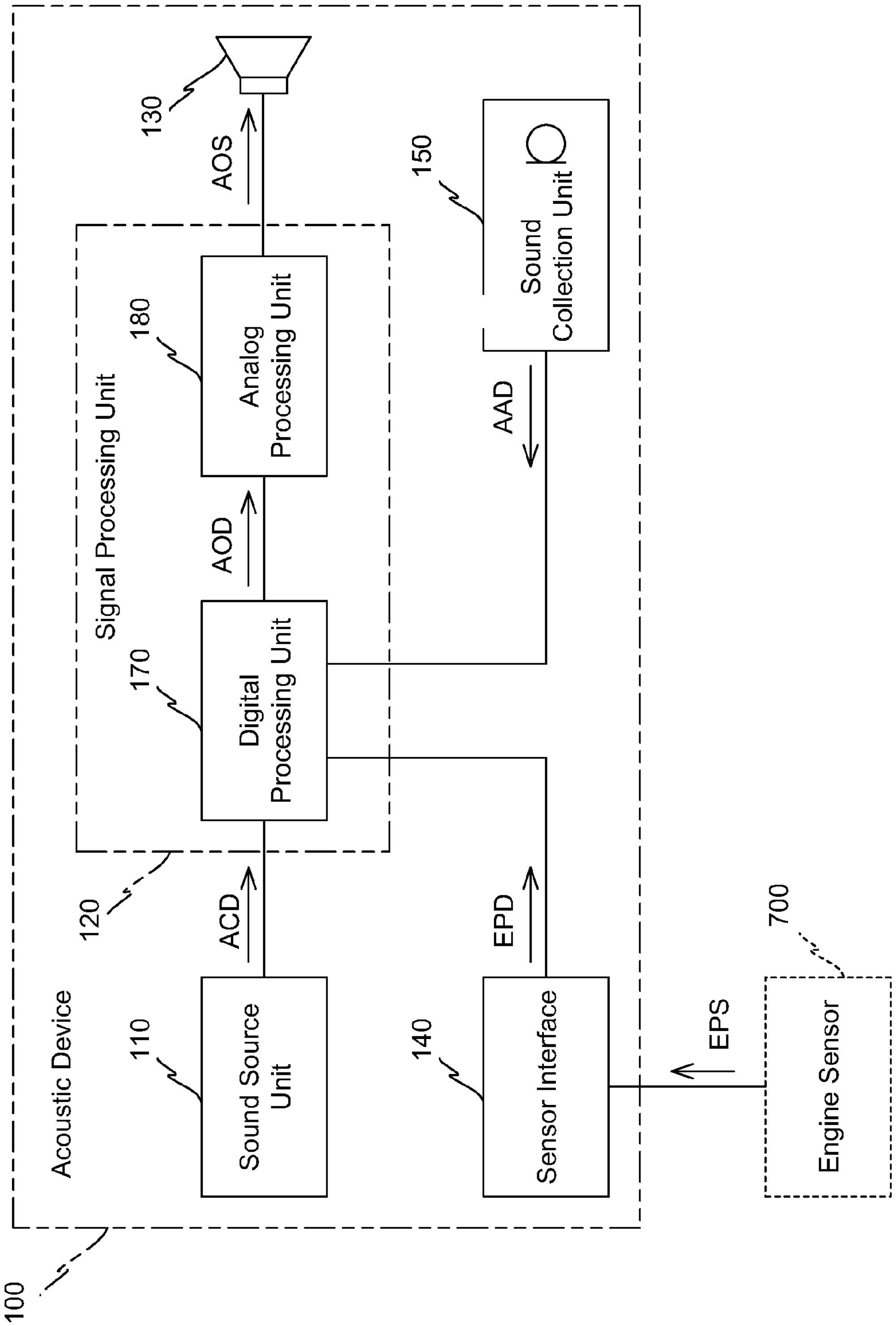
FIG. 1 is a block diagram, schematically showing the structure of an acoustic device according to an embodiment of the present invention.

In the following, an embodiment of the present invention will be explained with reference to FIGS. 1 through 7. It should be understood that, in the drawings, the same reference symbols are appended to elements that are the same or equivalent, and that duplicated explanation will be omitted.

[Structure]

In FIG. 1, the schematic structure of an acoustic device 100 according to an embodiment is shown as a block diagram. This acoustic device 100 is mounted to a vehicle that is driven by an engine.

As shown in this FIG. 1, the acoustic device 100 comprises a sound source unit 110, a signal processing unit 120, and a speaker 130. Moreover, the acoustic device 100 comprises a sensor interface 140 and a sound collection unit 150 that serves as a sound pickup means.

The sound source unit 110 mentioned above generates an audio signal ACD, which is a digital signal. For example, if the acoustic device 100 is a device that replays audio contents recorded upon a recording medium such as a compact disk (CD) or the like, then the sound source unit 110 comprises a reading means that reads the audio contents from that recording medium, and an extraction means that extracts the audio signal ACD from the results of reading by that reading means. Moreover, if the acoustic device 100 is a device that replays audio contents acquired by reception of a broadcast wave, then the sound source unit 110 comprises a contents extraction means that extracts the audio contents from the result of reception of a broadcast wave, and an audio signal extraction means that extracts the audio signal ACD from the results of extraction by that contents extraction means.

The signal processing unit 120 described above receives the audio signal ACD from the sound source unit 110. Moreover, the signal processing unit 120 receives a signal EPD from the sensor interface 140 and a signal AAD from the sound collection unit 150. And the signal processing unit 120 creates an output audio signal AOS on the basis of the signal EPD, the signal AAD, and the audio signal ACD. The output audio signal AOS that has been generated in this manner is sent to the speaker 130. The details of the structure of the signal processing unit 120 having the functions broadly described above will be recounted hereinafter.

The speaker 130 described above receives the output audio signal AOS from the signal processing unit 120. And the speaker 130 replays and outputs sound according to this output audio signal AOS.

The sensor interface 140 described above receives an engine pulse signal EPS from an engine sensor 700. And the sensor interface 140 converts the signal format of this engine pulse signal EPS so that it is compatible with the signal processing unit 120, and generates a signal EPD in digital format. The signal EPD that has been generated in this manner is sent to the signal processing unit 120.

The sound collection unit 150 described above is built to include a microphone. The result of sound pickup by this microphone is sent from the sound collection unit 150 to the signal processing unit 120 as a signal AAD in digital format.

Next, the signal processing unit 120 described above will be explained. This signal processing unit 120 comprises a digital processing unit 170 and an analog processing unit 180.

Figure 2:
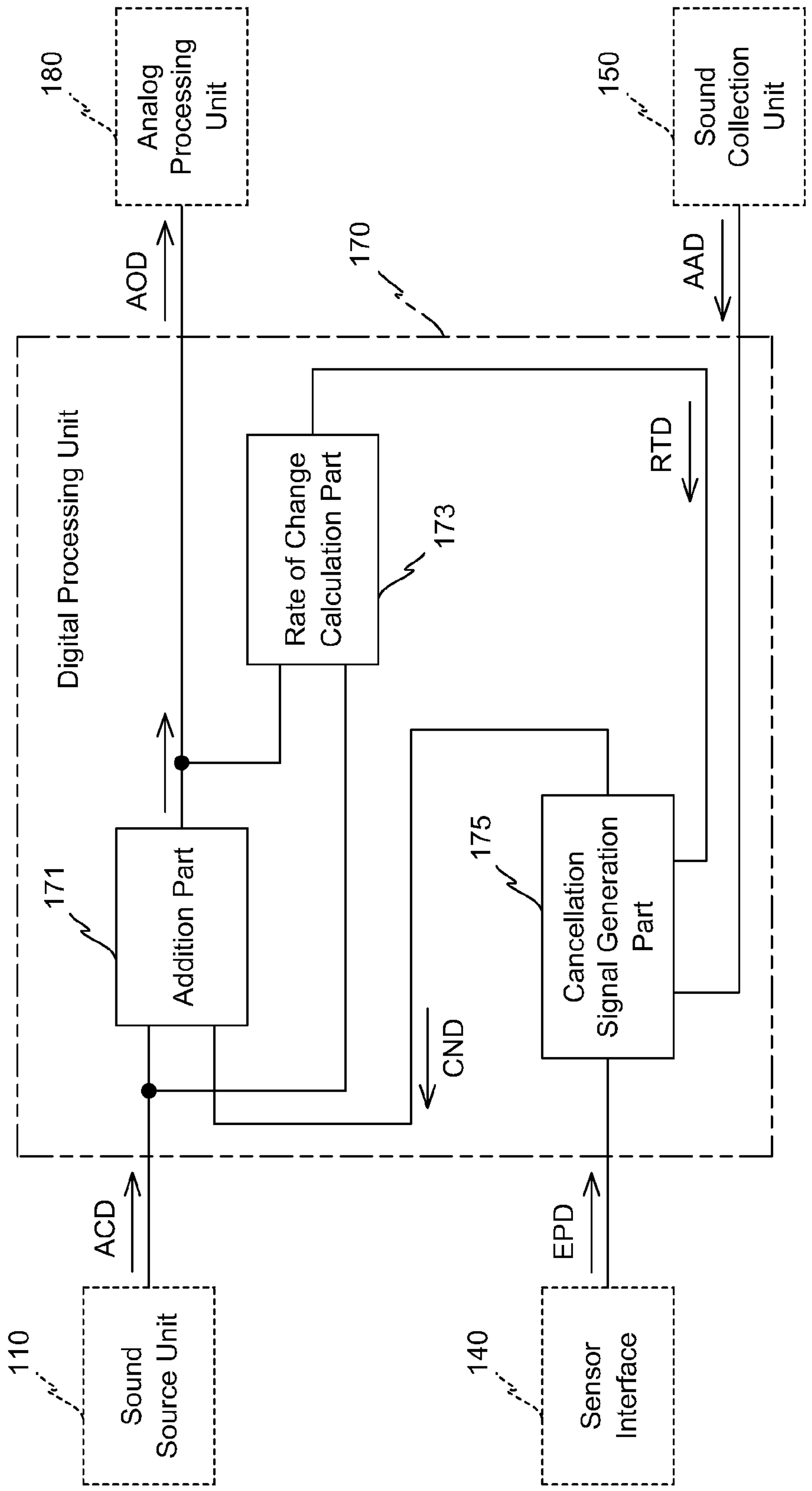
FIG. 2 is a block diagram showing the structure of a digital processing unit of FIG. 1.

The digital processing unit 170 described above generates a signal AOD in digital format on the basis of the audio signal ACD from the sound source unit 110, the signal EPD from the sensor interface 140, and the signal AAD from the sound collection unit 150. As shown in FIG. 2, this digital processing unit 170 having this function comprises an addition part 171 that serves as an addition means, a rate of change calculation part 173 that serves as a detection means, and a cancellation signal generation part 175 that serves as a generation means.

The addition part 171 described above receives the audio signal ACD from the sound source unit 110 and a cancellation signal CND from the cancellation signal generation part 175. And the addition part 171 adds together these two signals. The result of this addition is sent to the analog processing unit 180 and to the rate of change calculation part 173 as the signal AOD.

Figure 3:
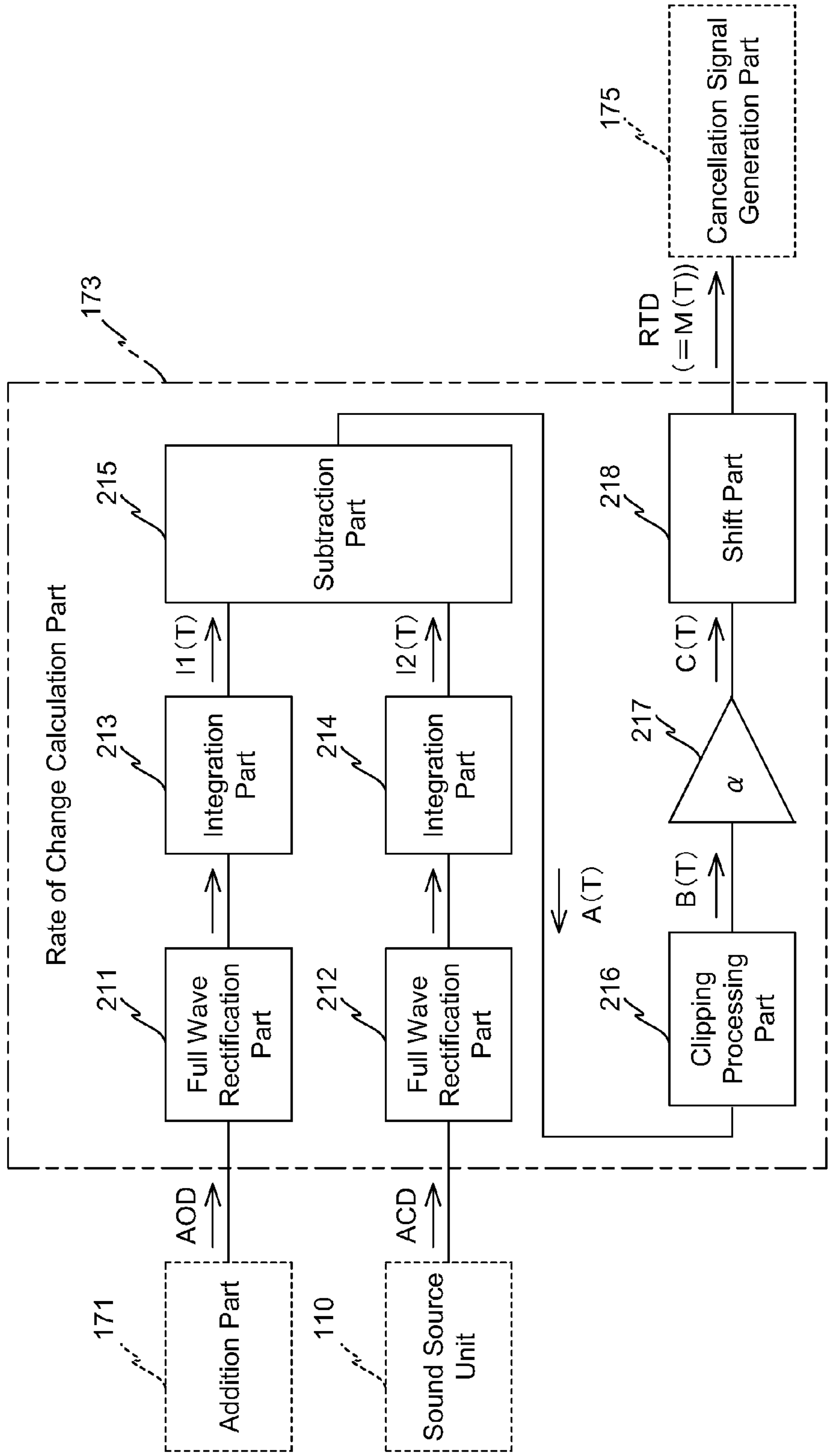
FIG. 3 is a block diagram showing the structure of a rate of change calculation part of FIG. 2.

The rate of change calculation part 173 detects a relationship between the signal level of the audio signal ACD and the signal level of the signal AOD, and calculates a rate of change parameter M(T) that is to be taken into consideration when the cancellation signal CND is being generated by the cancellation signal generation part 175. As shown in FIG. 3, the rate of change calculation part 173 having this function comprises full wave rectification parts 211 and 212, integration parts 213 and 214, and a subtraction part 215. Moreover, the rate of change calculation part 173 comprises a clipping processing part 216, a multiplication part 217, and a shift part 218.

The full wave rectification part 211 described above receives the signal AOD from the addition part 171. And the full wave rectification part 211 performs full wave rectification upon the signal AOD, and sends the result of this rectification to the integration part 213.

Moreover, the full wave rectification part 212 described above receives the audio signal ACD from the sound source unit 110. And the full wave rectification part 212 performs full wave rectification upon the audio signal ACD, and sends the result of this rectification to the integration part 214.

The integration part 213 described above obtains the signal level of the signal AOD by integrating the result of full wave rectification by the full wave rectification part 211 according to a predetermined time constant. And the integration part 213 sends a result of integration $I_1(T)$ to the subtraction part 215.

Moreover, in a similar manner to the case of the integration part 213, the integration part 214 described above obtains the signal level of the audio signal ACD by integrating the result of full wave rectification by the full wave rectification part 212 according to a predetermined time constant. And the integration part 214 sends a result of integration $I_2(T)$ to the subtraction part 215.

The predetermined time constant is determined in advance from the standpoint of generating an effective cancellation signal CND, on the basis of experiment, simulation, experience and so on.

The subtraction part 215 described above receives the result of integration $I_1(T)$ from the integration part 213 and the result of integration $I_2(T)$ from the integration part 214. And the subtraction part 215 subtracts the integration result $I_2(T)$ from the integration result $I_1(T)$. The result A(T) [$=I_1(T)-I_2(T)$] of this subtraction shows the level of influence of the cancellation signal CND upon the audio signal ACD. This subtraction result A(T) is sent from the subtraction part 215 to the clipping processing part 216.

The clipping processing part 216 described above receives the subtraction result A(T) from the subtraction part 215. And the clipping processing part 216 generates a clipping result B(T) from the subtraction result A(T). This clipping result B(T) that has been generated is sent from the clipping processing part 216 to the multiplication part 217.

Figure 4:
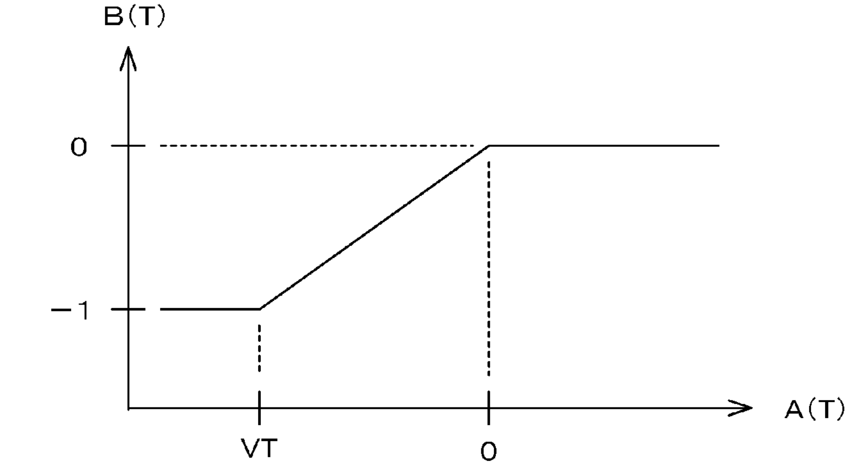
FIG. 4 is a graph showing a relationship between A(T) and B(T) in FIG. 2.

When generating this clipping result B(T), if the value of the subtraction result A(T) is greater than or equal to "0", then the clipping processing part 216 sets the value of the clipping result B(T) to "0". Moreover, if the value of the subtraction result A(T) is less than or equal to "VT (<0)", then the clipping processing part 216 sets the value of the clipping result B(T) to "−1". Furthermore, as the value of the subtraction result A(T) changes over the range of "VT"~"0", the clipping processing part 216 changes the clipping result B(T) over the range of "−1" to "0". This relationship between the value of the subtraction result A(T) and the clipping result B(T) is shown in FIG. 4.

Figure 5:
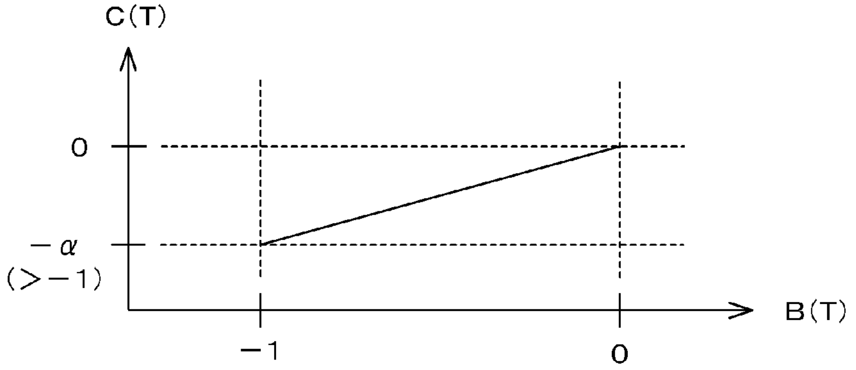
FIG. 5 is a graph showing a relationship between B(T) and C(T) in FIG. 2.

Returning to FIG. 3, the multiplication part 217 described above receives the clipping result B(T) from the clipping processing part 216. And the multiplication part 217 multiplies the clipping result B(T) by a constant α (where 0<α<1). The relationship between the clipping result B(T) and the multiplication result C(T) is shown in FIG. 5. This multiplication result C(T) is sent from the multiplication part 217 to the shift part 218.

It should be understood that the constant α is determined in advance on the basis of experiment, simulation, experience and so on, from the standpoint of generating a cancellation signal CND which allows noise control to take place without imparting any sense of discomfort to the listener.

Figure 6:
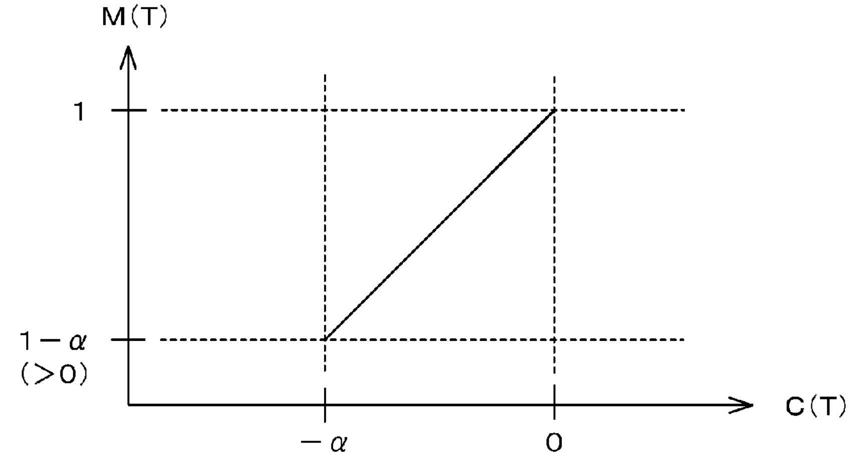
FIG. 6 is a graph showing a relationship between C(T) and M(T) in FIG. 2.

Returning to FIG. 3, the shift part 218 described above receives the multiplication result C(T) from the multiplication part 217. And the shift part 218 uniformly increases this multiplication result C(T) by just "1", thus calculating a rate of change parameter M(T) [=C(T)+1]. The relationship between the multiplication result C(T) and the rate of change parameter M(T) is shown in FIG. 6. Here, as generally shown in FIGS. 4 through 6, when a portion of the audio signal ACD is eliminated by adding the cancellation signal CND to the audio signal ACD, the greater this degree of cancellation is, the smaller does the rate of change parameter M(T) become. The rate of change parameter M(T) that has been obtained in this manner is taken as a signal RTD, and is sent from the shift part 218 to the cancellation signal generation part 175.

Figure 7:
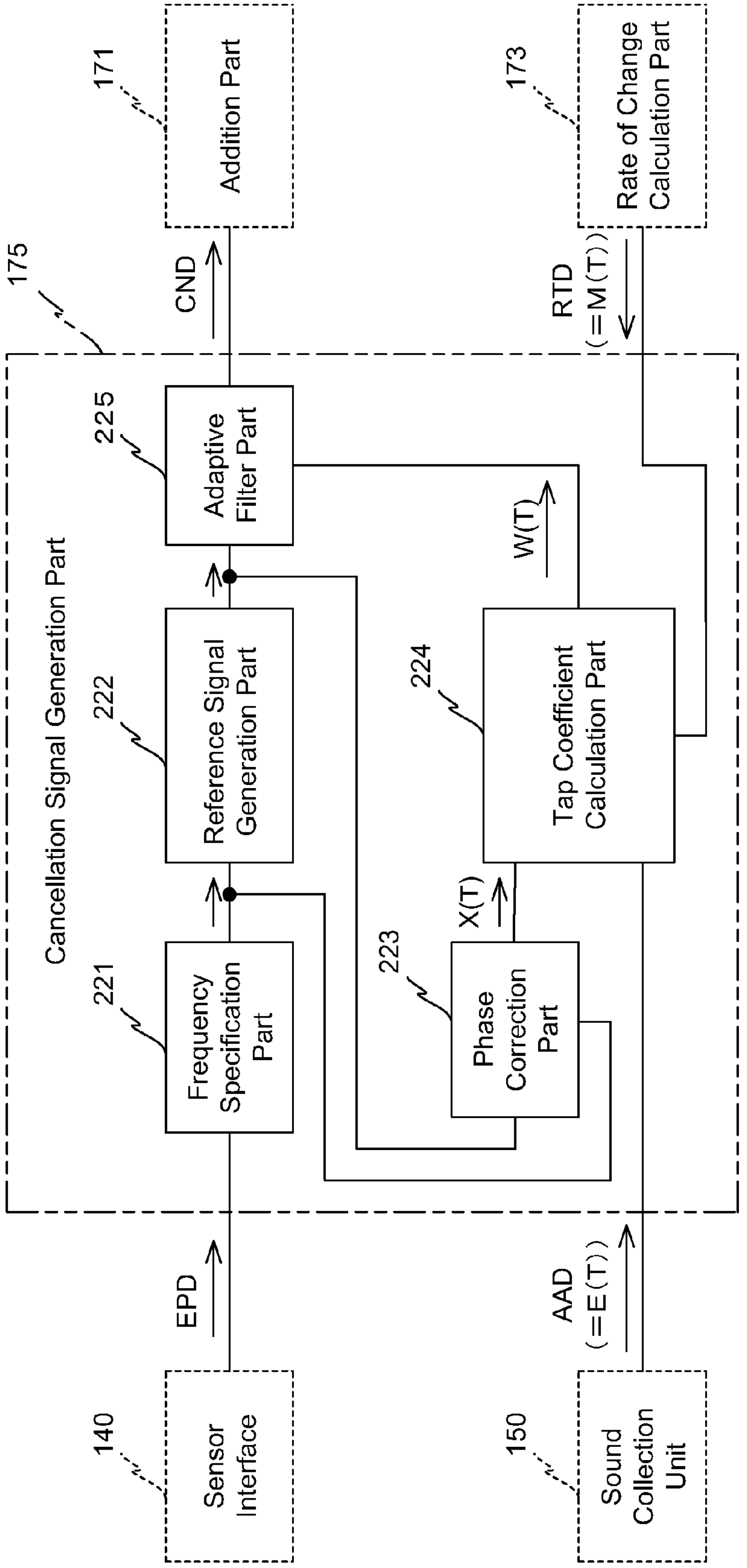
FIG. 7 is a block diagram showing the structure of a cancellation signal generation part of FIG. 2.

Returning to FIG. 2, the cancellation signal generation part 175 described above receives the signal EPD from the sensor interface 140, the signal AAD from the sound collection unit 150, and the signal RTD from the rate of change calculation part 173. And the cancellation signal generation part 175 generates the cancellation signal CND on the basis of these signals EPD, AAD, and RTD that it has received. As shown in FIG. 7, the cancellation signal generation part 175 having this function comprises a frequency specification part 221 that serves as a specification means, a reference signal generation part 222 that serves as a reference signal generation means, and a phase correction part 223. Moreover, the cancellation signal generation part 175 also comprises a tap coefficient calculation part 224 and an adaptive filter part 225. It should be understood that the phase correction part 223, the tap coefficient calculation part 224, and adaptive filter part 225 constitute a cancellation signal generation means.

The frequency specification part 221 described above receives the signal EPD from the sensor interface 140. And, on the basis of this signal EPD, the frequency specification part 221 detects the frequency of the engine pulses, which is the operating frequency of the engine. Next, the frequency specification part 221 specifies a frequency that is a predetermined number of times this detected frequency as being the frequency of the noise that is to be the subject of cancellation. The frequency that has been specified in this manner is sent to the reference signal generation part 222 and to the phase correction part 223.

It should be understood that this predetermined number is determined in advance on the basis of experiment, simulation, experience and so on, in consideration of the range of frequencies that the operating frequency of the engine can assume, the range of frequencies that the listener senses as being noise, and so on.

The reference signal generation part 222 described above receives the frequency specified by the frequency specification part 221. And the reference signal generation part 222 generates a reference signal of that specified frequency. It should be understood that in this embodiment, as the reference signal, the reference signal generation part 222 is adapted to generate reference signals of two types: a sine wave signal and a cosine wave signal. The reference signal generated by the reference signal generation part 222 in this manner is sent to the phase correction part 223 and to the adaptive filter part 225.

The phase correction part 223 described above receives the frequency specified by the frequency specification part 221 and the reference signal generated by the reference signal generation part 222. And after having outputted, on the basis of the specified frequency, a signal of the specified frequency from the speaker 130 and having picked it up with the sound collection unit 150, the phase correction part 223 obtains the transmission characteristics, including the delay time period until it arrives at the tap coefficient calculation part 224 as a signal from the sound collection unit 150. And, by employing these transmission characteristics that have thus been obtained, the phase correction part 223 corrects the phase of the reference signal so that it matches the phase at the time point that audio according to the reference signal arrives at the sound collection unit 150 when outputted from the speaker 130. The signal X(T) upon which phase correction has been performed in this manner is sent to the tap coefficient calculation part 224.

It should be understood that, in this embodiment, the phase correction part 223 is adapted to correct the phase for both of the two types of reference signal, i.e. both for the sine wave signal and for the cosine wave signal.

The tap coefficient calculation part 224 described above receives the signal X(T) from the phase correction part 223, the signal AAD (=E(T)) from the sound collection unit 150, and the signal RTD (=M(T)) from the rate of change calculation part 173. On the basis of these received signals and the tap coefficient W(T−τ) that it calculated in the previous cycle, the tap coefficient calculation part 224 calculates a new tap coefficient W(T) according to the following Equation (1):

$$W(T)=M(T)\cdot W(T-\tau)-\mu\cdot E(T)\cdot X(T) \quad (1)$$

Here, τ is the period of the tap coefficient calculation cycle, and μ is the step coefficient (<1).

Here, the greater the rate of change parameter M(T) is, the greater is the level of noise cancellation for which the tap coefficient W(T) is calculated. Due to this, since the rate of change parameter M(T) is at its maximum value (=1) if the signal level of the signal AOD that results from adding the cancellation signal CND to the audio signal ACD is larger than the signal level of the audio signal ACD, accordingly a tap coefficient W(T) is calculated for which the level of noise cancellation is the highest. On the other hand, if the signal level of the signal AOD that results from adding the cancellation signal CND to the audio signal ACD is smaller than the signal level of the audio signal ACD, then, the smaller the rate of change parameter M(T) is, the smaller becomes the level of noise cancellation for which the tap coefficient W(T) is calculated.

It should be understood that, in this embodiment, the tap coefficient calculation part 224 is adapted to calculate a tap coefficient for each of the two types of phase correction signal from the phase correction part 223. In other words, in this embodiment, the tap coefficient calculation part 224 is adapted to calculate tap coefficients of two types: a tap coefficient (hereinafter termed the coefficient $W_S(T)$) that corresponds to the sine wave signal generated by the reference signal generation part 222, and a tap coefficient (hereinafter termed the coefficient $W_C(T)$) that corresponds to the cosine wave signal generated by the reference signal generation part 222.

The adaptive filter part 225 described above receives the reference signal from the reference signal generation part 222 and the tap coefficient W(T) from the tap coefficient calculation part 224. And the adaptive filter part 225 performs processing upon the reference signal from the reference signal generation part 222 according to the tap coefficient W(T), and thereby generates the cancellation signal CND. The cancellation signal CND that has been generated in this manner is sent from the adaptive filter part 225 to the addition part 171.

It should be understood that, in this embodiment, the adaptive filter part 225 multiplies the sine wave signal generated by the reference signal generation part 222 by the coefficient $W_S(T)$. Moreover, it multiplies the cosine wave signal generated by the reference signal generation part 222 by the coefficient $W_C(T)$. And the adaptive filter part 225 is adapted to calculate the cancellation signal CND by adding together the results of these two multiplications.

Returning to FIG. 1, the analog processing unit 180 receives the signal AOD from the digital processing unit 170. And the analog processing unit 180 generates the output audio signal AOS on the basis of this signal AOD, and sends it to the speaker 130. The analog processing unit 180 having this function comprises a D/A (Digital to Analog) conversion part not shown in the figures and a power amplification part, neither of which is shown in the figures.

The D/A conversion part mentioned above includes a D/A converter. This D/A conversion part receives the signal AOD from the digital processing unit 170. And the D/A conversion part converts the signal AOD to an analog signal. The result of D/A conversion by the D/A conversion part is sent to the power amplification part.

The power amplification part mentioned above receives the result of D/A conversion by the D/A conversion part. And the power amplification part power amplifies this D/A conversion result. Then the result of this amplification by the power amplification part is sent to the speaker 130 as the output audio signal AOS.

[Operation]

Next, the operation of the acoustic device 100 having the structure as described above will be explained.

As a preliminary, it will be supposed that the frequency specification part 221 of the cancellation signal generation part 175 in the digital processing unit 170 is receiving the signal EPD from the sensor interface 140. Furthermore, it will be supposed that the sound collection unit 150 is performing sound pickup operation, and that it is reporting the results of its pickup of sound to the cancellation signal generation part 175 as the signal AAD.

When the audio signal ACD is outputted from the sound source unit 110, processing is performed upon this audio signal ACD by the signal processing unit 120 on the basis of the signal EPD and the signal AAD received respectively from the sensor interface 140 and the sound collection unit 150 that is operating together with the sound source unit 110. In this signal processing unit 120, the audio signal ACD is received by the addition part 171 of the digital processing unit 170 and by the rate of change calculation part 173 (refer to FIG. 2).

Upon receipt of the audio signal ACD, the addition part 171 adds together this audio signal ACD and the cancellation signal CND that, at this time point, is being generated by the cancellation signal generation part 175. The result of this addition by the addition part 171 is sent to the analog processing unit 180 and to the rate of change calculation part 173 as the signal AOD.

Upon receipt of the signal AOD and the audio signal ACD, the rate of change calculation part 173 detects the relationship between the signal level of the signal AOD and the signal level of the audio signal ACD, and calculates the rate of change parameter M(T) that is to be taken into consideration during the generation of the cancellation signal CND by the cancellation signal generation part 175. For this rate of change parameter M(T), in the rate of change calculation part 173, the full wave rectification part 211 that receives the signal AOD full wave rectifies this signal AOD. And the integration part 213 obtains the signal level of the signal AOD by integrating the result of rectification by the full wave rectification part 211 according to the predetermined time constant, and sends the integration result $I_1(T)$ to the subtraction part 215 (refer to FIG. 3).

Moreover, the full wave rectification part 212 that receives the audio signal ACD full wave rectifies this audio signal ACD. And the integration part 214 obtains the signal level of the audio signal ACD by integrating the result of rectification by the full wave rectification part 212 according to the predetermined time constant, and sends the integration result $I_2(T)$ to the subtraction part 215 (refer to FIG. 3).

Upon receipt of the integration result $I_1(T)$ and the integration result $I_2(T)$, the subtraction part 215 subtracts the integration result $I_2(T)$ from the integration result $I_1(T)$, and sends the result of subtraction A(T) $[=I_1(T)-I_2(T)]$ to the clipping processing part 216. And, upon receipt of this subtraction result A(T), the clip processing part 216 generates the clipping result B(T) from the subtraction result A(T) (refer to FIG. 4), and sends it to the multiplication part 217 (refer to FIG. 3).

Upon receipt of this clipping result B(T), the multiplication part 217 multiplies the clipping result B(T) by the constant $\alpha$ (where $0<\alpha<1$), and sends the multiplication result C(T) to the shift part 218. And, upon receipt of this multiplication result C(T), the shift part 218 uniformly increases the multiplication result C(T) by "1" and thereby calculates the rate of change parameter M(T) [=C(T)+1], and sends this to the cancellation signal generation part 175 as the signal RTD (refer to FIG. 3).

Upon receipt of the rate of change parameter M(T), the cancellation signal generation part 175 generates a new cancellation signal CND while taking into consideration the signal EPD from the sensor interface 140 and the signal AAD from the sound collection unit 150. When generating this cancellation signal CND, in the cancellation signal generation part 175, the frequency specification part 221 that has received the signal EPD detects the frequency of the engine pulses, which is the operating frequency of the engine, on the basis of this signal EPD, and specifies a frequency that is the predetermined number of times this detected frequency as being the frequency of the noise that is to be the subject for cancellation. The frequency that has been specified in this manner is sent to the reference signal generation part 222 and to the phase correction part 223 (refer to FIG. 7).

Upon receipt of this frequency that has been specified by the frequency specification part 221, the reference signal generation part 222 generates a reference signal of that specified frequency, and sends it to the phase correction part 223 and to the adaptive filter part 225. And, upon receipt of this reference signal and of the frequency that has been specified by the frequency specification part 221, and after a signal of that specified frequency has been outputted from the speaker 130 on the basis of that specified frequency and this signal has been picked up by the sound collection unit 150, the phase correction part 223 obtains the transmission characteristics of this signal, including the delay time until it arrives at the tap coefficient calculation part 224 as a signal from the sound collection unit 150, and, using these transmission characteristics that have thus been obtained, corrects the phase of the reference signal so that it agrees in phase at the time point that audio according to the reference signal arrives at the sound collection unit 150 when outputted from the speaker 130. This signal X(T) upon which phase correction has been performed is sent to the tap coefficient calculation part 224 (refer to FIG. 7).

Upon receipt of this signal X(T), the tap coefficient calculation part 224 calculates a new tap coefficient W(T) according to Equation (1) described above, while taking into consideration the signal X(T) from the phase correction part 223, the signal AAD (=E(T)) from the sound collection unit 150, and the signal RTD (=M(T)) from the rate of change calculation part 173. The new tap coefficient W(T) that has been calculated in this manner is sent to the adaptive filter part 225 (refer to FIG. 7).

Upon receipt of this tap coefficient W(T), the adaptive filter part 225 performs processing according to this tap coefficient W(T) upon the reference signal from the reference signal generation part 222, and thus generates the cancellation signal CND. The cancellation signal CND that has been generated in this manner is sent to the addition part 171 (refer to FIG. 7).

Upon receipt of this newly generated cancellation signal CND, the addition part 171 adds together this newly generated cancellation signal CND and the audio signal ACD. The result of this addition by the addition part 171 is sent to the analog processing unit 180 and to the rate of change calculation part 173 as the new signal AOD (refer to FIG. 2).

Upon receipt by the analog processing unit 180 of this signal AOD from the digital processing unit 170, first, the D/A conversion part converts the signal AOD into an analog signal. Next, the power amplification part power amplifies this signal resulting from analog conversion, thus generating the output audio signal AOS that is sent to the speaker 130 (refer to FIG. 1). And the speaker 130 outputs replayed audio according to this output audio signal AOS from the analog processing unit 180.

As has been explained above, in this embodiment, during the generation of the cancellation signal CND, the rate of change calculation part 173 detects the relationship between the signal level of the audio signal ACD from the sound source unit 110 and the signal level of the signal AOD that is the result of addition together of that audio signal ACD and of the noise cancellation signal CND that is being generated at this time point in order to cancel out noise. The rate of change calculation part 173 calculates the rate of change parameter M(T) on the basis of this detected relationship between the levels of these signals.

Here, if the signal level of the signal AOD that results from the cancellation signal CND being added to the audio signal ACD is higher than the signal level of the audio signal ACD, then the rate of change calculation part 173 calculates the maximum value (=1) as being the rate of change parameter M(T) so as to indicate that the level of noise cancellation must be the highest possible. On the other hand, if the signal level of the signal AOD that results from the cancellation signal CND being added to the audio signal ACD is lower than the signal level of the audio signal ACD, then it calculates the rate of change parameter M(T) so as to indicate that, the greater the difference between these two signal levels is, the lower is the level of noise cancellation to be.

Upon receipt of this rate of change parameter M(T), the cancellation signal generation part 175 generates the cancellation signal CND while taking the value of the rate of change parameter M(T) into consideration, and sends it to the addition part 171. And the addition part 171 adds together the audio signal ACD and the cancellation signal CND, and outputs the result of this addition to the analog processing unit 180.

Thus since, according to this embodiment, the cancellation signal CND is generated while taking into consideration the relationship between the signal level of the audio signal ACD from the sound source, and the signal level of the signal AOD that results from adding the noise cancellation signal CND to that audio signal ACD, accordingly it is possible to suppress the creation of any sense of discomfort for the listener who is listening to the replayed audio contents, so that it is possible to perform appropriate noise control in a simple manner.

Moreover since, if the signal level of the signal AOD that results from adding the noise cancellation signal CND to the audio signal ACD is smaller than the signal level of the audio signal ACD from the sound source, then the level of noise cancellation is made to be the smaller, the greater is the difference between these two signal levels, accordingly it is possible to reduce the amount of cancellation of the audio signal ACD due to the cancellation signal CND being added to that audio signal ACD, so that it is possible to suppress the creation of any sense of discomfort for the listener who is listening to the replayed audio contents, and it is possible to perform appropriate noise control in a simple manner.

Modification of the Embodiment

The present invention is not to be considered as being limited to the embodiment described above; various alterations can be made thereto.

For example in the embodiment described above it is arranged, after having calculated the difference between the signal level of the signal AOD and the signal level of the audio signal ACD as a measure of the degree of influence of the cancellation signal CND upon the audio signal ACD, to perform the clip processing upon the result of this calculation. By contrast, it would also be acceptable to arrange, after having calculated the ratio between the signal level of the signal AOD and the signal level of the audio signal ACD as a measure of the degree of influence of the cancellation signal CND upon the audio signal ACD, to perform the clip processing upon the result of this calculation.

Furthermore, it would also be acceptable to arrange to extract from the audio signal ACD the component that has the frequency of the subject for noise cancellation as specified from the engine pulses, and to detect the result of this extraction as a measure of the degree of influence of the cancellation signal CND upon the audio signal ACD.

Moreover while, in the embodiment described above, the operating noise of the engine was taken as being the noise to be cancelled, it would also be acceptable to arrange to perform noise control upon the noise such as the operating noise of some other device that is mounted to the vehicle, a load noise, a noise from a blower, or the like.

Yet further while, in the embodiment described above, the present invention was applied to an acoustic device that is mounted to a vehicle, it would also be acceptable to arrange to apply the present invention to an acoustic device that is mounted to some moving body other than a vehicle. Even further, the present unit is not limited in its application to a moving body such as a vehicle or the like; it would also be acceptable to arrange to apply the present invention to an acoustic device that is installed in a dwelling or the like.

It should be understood that it would also be acceptable to arrange to execute all or a portion of the processing of the embodiment described above, by building the digital processing unit 170 of the embodiment described above as a computer that serves as a calculation means and that incorporates a DSP (Digital Signal Processor) and so on, and by executing a program that is prepared in advance upon that computer. This program could be recorded upon a recording medium that can be read by a computer, such as a hard disk, a CD-ROM, a DVD or the like, and could be executed by being read out from that recording medium by the computer. Moreover, it would also be possible to arrange for this program to be acquired in the format of being recorded upon a transportable recording medium such as a CD-ROM, a DVD or the like, or to arrange for it to be acquired in the format of being distributed via a network such as the internet or the like.

The invention claimed is:

1. An acoustic device that outputs audio from a speaker to a predetermined space, comprising:

an addition part configured to add together a first audio signal from a sound source and a noise cancellation signal for calculating a second audio signal to be supplied to said speaker;

a detection part configured to detect a signal level of said first audio signal and a signal level of said second audio signal;

a sound pickup part configured to pick up sound that has arrived at a predetermined position within said predetermined space; and a generation part configured to generate said noise cancellation signal by referring to a relationship between results of detection by said detection part and to a result of sound pickup by said sound pickup part, wherein the relationship between results is one of a difference between said first audio signal and said second audio signal and a ratio of the signal level of said first audio signal to the signal level of said second audio signal, wherein when the signal level of said second audio signal is smaller than the signal level of said first audio signal and the relationship between results is the difference between said first audio signal and said second audio signal, the greater the difference, the smaller an amount of noise cancellation performed by said generation part, and wherein when the signal level of said second audio signal is smaller than the signal level of said first audio signal and the relationship between results is the ratio of the signal level of said first audio signal to the signal level of said second audio signal, the smaller the ratio, the smaller an amount of noise cancellation performed by said generation part.

2. An acoustic device according to claim 1, said generation part comprising:

a specification part configured to specify a cancellation subject frequency on the basis of the operating cycle of a predetermined device that is operating cyclically and is a noise sound source;

a reference signal generation part configured to generate a reference signal having said specified cancellation subject frequency; and a cancellation signal generation part configured to generate said noise cancellation signal on the basis of said reference signal, the relationship between the results of detection by said detection part, the result of sound pickup by said sound pickup, and transmission characteristics from said speaker to said predetermined position.

3. An acoustic device according to claim 2, being mounted to a moving body, and in that said predetermined device is an engine device that generates drive power for said moving body.

4. A noise control method used by an acoustic device that outputs audio from a speaker to a predetermined space, comprising:

an addition process of, by adding together a first audio signal from a sound source and a noise cancellation signal, calculating a second audio signal to be supplied to said speaker;

a detection process of detecting a signal level of said first audio signal and a signal level of said second audio signal;

a sound pickup process of picking up sound that has arrived at a predetermined position within said predetermined space; and a generation process of generating said noise cancellation signal by referring to a relationship between the result of detection by said detection process and to the result of sound pickup by said sound pickup process, wherein the relationship between results is one of a difference between said first audio signal and said second audio signal and a ratio of the signal level of said first audio signal to the signal level of said second audio signal, wherein when the signal level of said second audio signal is smaller than the signal level of said first audio signal and the relationship between results is the difference between said first audio signal and said second audio signal, the greater the difference, the smaller an amount of noise cancellation performed by said generation part, and wherein when the signal level of said second audio signal is smaller than the signal level of said first audio signal and the relationship between results is the ratio of the signal level of said first audio signal to the signal level of said second audio signal, the smaller the ratio, the smaller an amount of noise cancellation performed by said generation part.

5. A non-transient computer-readable medium having recorded therein a noise control program that, when executed, causes a calculation part to execute the noise control method as described in claim 4.

* * * * *